United States Patent
Cannell et al.

(10) Patent No.: US 11,932,587 B2
(45) Date of Patent: Mar. 19, 2024

(54) METHOD OF CAUSING CONVERSION OF VOLATILE TERPENE SPECIES

(71) Applicant: Givaudan SA, Vernier (CH)

(72) Inventors: Jonathon Cannell, Cincinnati, OH (US); Chad Allen Hansen, Lebanon, OH (US); Andrew Finn, Milford, OH (US); Geoff Marshall-Hill, Newport Pagnell (GB)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 18/032,075

(22) PCT Filed: Oct. 28, 2021

(86) PCT No.: PCT/EP2021/080008
§ 371 (c)(1),
(2) Date: Apr. 14, 2023

(87) PCT Pub. No.: WO2022/090402
PCT Pub. Date: May 5, 2022

(65) Prior Publication Data
US 2023/0286883 A1    Sep. 14, 2023

Related U.S. Application Data

(60) Provisional application No. 63/107,874, filed on Oct. 30, 2020.

(51) Int. Cl.
*C07C 1/22* (2006.01)
*C07C 7/04* (2006.01)

(52) U.S. Cl.
CPC .................. *C07C 1/22* (2013.01); *C07C 7/04* (2013.01); *C07C 2527/20* (2013.01); *C07C 2602/28* (2017.05)

(58) Field of Classification Search
CPC ......... C07C 1/22; C07C 7/04; C07C 2527/20; C07C 2602/28
See application file for complete search history.

(56) References Cited

FOREIGN PATENT DOCUMENTS

| WO | 2016/029153 A1 | 2/2016 |
|---|---|---|
| WO | 2016/029187 A2 | 2/2016 |

OTHER PUBLICATIONS

Davies A G, et al., "The Rearrangement of Allylic Hydroperoxidases Derived From (+) Valencene", Journal of the Chemical Society, Jan. 1, 1989, pp. 825-830.
Carole Gavira, et al., "Challenges and pitfalls of P450-dependent (+)- valencene bioconversion by *Saccharomyces cerevisiae*", Metabolic Engineering, Jul. 1, 2013, vol. 18, pp. 25-35.
International Search Report for Application No. PCT/EP2021/080008, dated Feb. 14, 2022.
International Written Opinion for Application No. PCT/EP2021/080008, dated Feb. 14, 2022.

*Primary Examiner* — Thuan D Dang
(74) *Attorney, Agent, or Firm* — Curatolo Sidoti & Trillis Co., LPA; Salvatore A. Sidoti; Floyd Trillis, III

(57) ABSTRACT

The conversion of nootkatol to nootkatene in a terpene blend is intentionally caused by adding a catalytically effective amount of at least one compound that catalyzes the reaction of nootkatol to nootkatene to the terpene blend containing nootkatol. Methods of preparing terpene blends, terpene blends, flavour compositions containing the terpene blends, beverages and foodstuffs containing the flavour compositions, fragrance compositions containing the terpene blends, and fragranced products containing the fragrance composition are also disclosed.

10 Claims, No Drawings

METHOD OF CAUSING CONVERSION OF VOLATILE TERPENE SPECIES

CROSS REFERENCE TO RELATED APPLICATIONS

This application is a national stage application of International Application No. PCT/EP2021/080008, filed 28 Oct. 2021, which claims priority from U.S. Provisional Patent Application No. 63/107,874, filed 30 Oct. 2020, both of which applications are incorporated herein by reference.

TECHNICAL FIELD

The present disclosure relates to methods for causing the conversion of volatile terpenes present in a terpene blend into desired terpene compounds. The present disclosure more particularly relates to methods for causing or inducing the conversion of nootkatols present in a blend of volatile terpenes into desired levels of nootkatene, methods of making terpene blends containing desired levels of nootkatols and nootkatene, terpene blends containing desired levels of nootkatols and nootkatene, and beverage, foodstuffs and fragrance products containing the terpene blends.

BACKGROUND

Nootkatone is a volatile essential oil blend that is derived from grapefruit and Alaska yellow cedar trees. Nootkatone oil blends are commonly used as citrus flavouring agents for food and beverages and as fragrance ingredients. With respect to food and beverage products, the α-nootkatol molecule is widely recognized as a key component in nootkatone oil blends, as the α-nootkatol contributes to the acceptable organoleptic profile of nootkatone oil blends.

Terpene blends currently demanded in the market contain little or no nootkatene. To address potential future shift in demand for terpene blends containing higher levels of nootkatene there is a need in the art for a method for processing raw material terpene blends to achieve desired levels of both nootkatol and nootkatene.

SUMMARY

Provided is a method of causing or inducing the conversion of nootkatol to nootkatene comprising providing a feed containing at least one nootkatol and treating the feed to cause or induce conversion of a portion of the nootkatol in the feed to nootkatene.

According to certain illustrative embodiments, the method of causing or inducing the conversion of nootkatol to nootkatene comprises providing a feed containing at least one nootkatol, treating the feed with at least one compound that catalyzes the conversion of the nootkatol to nootkatene, and subjecting the treated feed to reaction conditions effective to cause or induce conversion of at least a portion of the nootkatol in the feed to nootkatene.

According to certain illustrative embodiments, provided is a method of causing or inducing the conversion of nootkatol to nootkatene comprising providing a feed containing nootkatol, and adding a catalytically effective amount of at least one compound that catalyzes the conversion of nootkatol to nootkatene to the feed.

According to certain illustrative embodiments, also provided is a method of preparing a terpene blend comprising providing a feed containing at least one nootkatol, treating the feed to cause or induce conversion of nootkatol to nootkatene, and carrying out fractional distillation on the reacted feed.

According to certain illustrative embodiments, the method of preparing a terpene blend comprises providing a feed containing at least one nootkatol and optionally at least one compound that catalyzes the conversion of at least a portion of the nootkatol to nootkatene, treating the feed with at least one compound that catalyzes the conversion of nootkatol to nootkatene, and subjecting the treated feed to reaction conditions effective to cause or induce conversion of at least a portion of the nootkatol to nootkatene.

According to certain illustrative embodiments, the method of preparing a terpene blend comprises providing a feed containing at least one nootkatol and optionally at least one compound that catalyzes the conversion of the nootkatol to nootkatene, treating the feed with at least one acid compound that catalyzes the conversion of nootkatol to nootkatene, and carrying out fractional distillation on the reacted feed.

According to certain illustrative embodiments, the terpene blend is prepared in accordance with the method comprising providing a feed containing at least one nootkatol, treating the feed to cause or induce conversion of at least a portion of the nootkatol in the feed to nootkatene, and carrying out fractional distillation on the treated feed.

According to certain embodiments, provided is a terpene blend prepared in accordance with the method comprising providing a feed containing at least one nootkatol, treating the feed with a compound that causes or induces conversion of nootkatol to nootkatene, and subjecting the treated feed to reaction conditions effective to cause or induce conversion of at least a portion of the nootkatol in the treated feed to nootkatene.

According to certain embodiments, the terpene blend is prepared in accordance with the method comprising providing a feed containing at least one nootkatol and optionally at least one compound that catalyzes the conversion of nootkatol to nootkatene, treating the feed with at least one compound that catalyzes the conversion of nootkatol to nootkatene, and subjecting the treated feed to reaction conditions effective to cause or induce conversion of at least a portion of the nootkatol in the feed to nootkatene.

According to certain illustrative embodiments, the terpene blend is prepared in accordance with the method comprising providing a feed containing at least one nootkatol and optionally at least one compound that catalyzes the conversion of nootkatol to nootkatene, treating the feed with at least one acid compound that catalyzes the conversion of nootkatol to nootkatene, and carrying out fractional distillation on the treated feed.

According to certain illustrative embodiments, provided is a beverage or foodstuff comprising a beverage or foodstuff base and a terpene blend prepared by providing a feed containing at least one nootkatol, treating the feed with a compound that causes or induces conversion of the at least one nootkatol to nootkatene, and carrying out fractional distillation on the treated feed.

According to certain illustrative embodiments, provided is a beverage or foodstuff comprising a beverage or foodstuff base and a terpene blend prepared by providing a feed containing at least one nootkatol, treating the feed with a compound that causes or induces conversion of nootkatol to nootkatene, and subjecting the treated feed to reaction conditions effective to cause or induce conversion of at least a portion of the nootkatol in the feed to nootkatene.

According to certain illustrative embodiments, provided is a beverage or foodstuff comprising a beverage or foodstuff base and a terpene blend prepared by providing a feed containing at least one nootkatol and optionally at least one compound that catalyzes the conversion of the nootkatol to nootkatene, treating the feed with at least one compound that catalyzes the conversion of nootkatol to nootkatene, and subjecting the treated feed to reaction conditions effective to cause or induce conversion of at least a portion of the nootkatol in the treated feed to nootkatene According to certain illustrative embodiments, provided is a beverage or foodstuff comprising a beverage or foodstuff base and a terpene blend prepared by providing a feed containing at least one nootkatol and optionally at least one compound that catalyzes the conversion of nootkatol to nootkatene, treating the feed with at least one acid compound that catalyzes the conversion of nootkatol to nootkatene, and carrying out fractional distillation on the reacted feed.

According to certain illustrative embodiments, provided is a fragrance product comprising a fragrance product base and a terpene blend prepared by providing a feed containing at least one nootkatol, treating the feed with a compound that causes or induces conversion of nootkatol to nootkatene, and carrying out fractional distillation on the treated feed.

According to certain illustrative embodiments, provided is a fragrance product comprising a fragrance product base and a terpene blend prepared by providing a feed containing at least one nootkatol, treating the feed with a compound that causes or induces conversion of nootkatol to nootkatene, and subjecting the treated feed to reaction conditions effective to cause or induce conversion of at least a portion nootkatol to nootkatene.

According to certain illustrative embodiments, provided is a fragrance product comprising a fragrance product base and a terpene blend prepared by providing a feed containing at least one nootkatol and optionally at least one compound that catalyzes the conversion of nootkatol to nootkatene, treating the feed with at least one compound that catalyzes the conversion of nootkatol to nootkatene, and carrying out fractional distillation on the treated feed.

According to certain illustrative embodiments, provided is a fragrance product comprising a fragrance product base and a terpene blend prepared by providing a feed containing nootkatol and optionally at least one compound that catalyzes the conversion of nootkatol to nootkatene, treating the feed with at least one acid compound that catalyzes the conversion of nootkatol to nootkatene, and subjecting the treated feed to reaction conditions effective to cause or induce conversion of at least a portion of the nootkatol to nootkatene.

Use of a terpene blend as a fragrance in a fragrance composition or fragranced product is also provided, the terpene blend prepared by providing a feed containing at least one nootkatol, treating the feed with a compound that causes or induces conversion of nootkatol to nootkatene, and carrying out fractional distillation on the treated feed.

Use of a terpene blend as a fragrance in a fragrance composition or fragranced product is also provided, the terpene blend prepared by providing a feed containing at least one nootkatol, treating the feed with a compound that causes or induces conversion of nootkatol to nootkatene, and subjecting the treated feed to reaction conditions effective to cause or induce conversion of at least a portion of the nootkatol in the treated feed to nootkatene.

Use of a terpene blend as a fragrance in a fragrance composition or fragranced product is also provided, the terpene blend prepared by providing a feed containing at least one nootkatol and optionally at least one compound that catalyzes the conversion of nootkatol to nootkatene, treating the feed with at least one compound that catalyzes the conversion of nootkatol to nootkatene, and subjecting the treated feed to reaction conditions effective to cause or induce conversion of a portion of the nootkatol in the treated feed to nootkatene.

Use of a terpene blend as a fragrance in a fragrance composition or fragranced product is also provided, the terpene blend prepared by providing a feed containing at least one nootkatol and optionally at least one compound that catalyzes the conversion of nootkatol to nootkatene, treating the feed with at least one acid compound that catalyzes the conversion of nootkatol to nootkatene, and carrying out fractional distillation on the treated feed.

Also disclosed is a fragrance composition comprising the terpene blend prepared in accordance with the presently disclosed methods and a fragrance base.

Also disclosed is a fragranced product comprising the terpene blend prepared in accordance with the presently disclosed methods or a fragrance composition comprising the terpene blend, and a fragrance product base.

Also disclosed is a method of prepared a fragranced product comprising mixing together the terpene blend prepared in accordance with the presently disclosed methods, or a fragrance composition comprising the terpene blend, with a fragrance product base.

Use of a terpene blend as a flavour in a food or beverage product is also provided, the terpene blend prepared by providing a feed containing at least one nootkatol, treating the feed with a compound that causes or induces conversion of nootkatol to nootkatene, and carrying out fractional distillation on the treated feed.

Use of a terpene blend as a flavour in a food or beverage product is also provided, the terpene blend prepared by providing a feed containing at least one nootkatol, treating the feed with a compound that causes or induces conversion of nootkatol to nootkatene, and subjecting the treated feed to reaction conditions effective to cause or induce conversion of at least a portion of the nootkatol in the treated feed to nootkatene.

Use of a terpene blend as a flavour in a food or beverage product is also provided, the terpene blend prepared by providing a feed containing at least one nootkatol and optionally at least one compound that catalyzes the conversion of nootkatol to nootkatene, treating the feed with at least one compound that catalyzes the conversion of nootkatol to nootkatene, and subjecting the treated feed to reaction conditions effective to cause or induce conversion of at least a portion of the nootkatol in the feed to nootkatene.

Use of a terpene blend as a flavour in a food or beverage product is also provided, the terpene blend prepared by providing a feed containing at least one nootkatol and optionally at least one compound that catalyzes the conversion of nootkatol to nootkatene, treating the feed with at least one acid compound that catalyzes the conversion of nootkatol to nootkatene, and carrying out fractional distillation on the reacted feed.

Also disclosed is a flavour composition comprising the terpene blend prepared in accordance with the presently disclosed methods and a flavour base.

Also disclosed is a food or beverage product comprising the terpene blend prepared in accordance with the presently disclosed methods or a flavour composition comprising the terpene blend, and a flavour product base.

Also disclosed is a method of preparing a food or beverage product comprising mixing together the terpene blend prepared in accordance with the presently disclosed methods, or a flavour composition comprising the terpene blend, with a food or beverage product base.

DETAILED DESCRIPTION

Raw material terpene blends may contain nootkatols. As used in this specification, the term "nootkatol" includes α-nootkatol and β-nootkatol. According to certain embodiments, the raw material terpene blend includes at least one nootkatol. According to illustrative embodiments, the raw material terpene blend comprises α-nootkatol. According to other illustrative embodiments, the raw material terpene blend comprises β-nootkatol. According to further illustrative embodiments, the raw material terpene blend comprises both α-nootkatol and β-nootkatol. Certain compounds, such as acid compounds, catalyze the reaction of nootkatol to nootkatene at elevated temperatures utilized in typical fractional distillation processes conducted on the raw material terpene blend to prepare nootkatone blends for use as flavour or fragrance ingredients. Disclosed is a method for causing or inducing the conversion of nootkatol, such as α-nootkatol, present in a blend of terpenes to nootkatene.

According to certain embodiments, the raw material terpene blend used in accordance with the presently disclosed methods contains at least α-nootkatol. According to certain illustrative embodiments, the raw material terpene blend may comprise more than one nootkatol, such as a mixture of α-nootkatol and β-nootkatol. According to further illustrative embodiments, the raw material blend may comprise α-nootkatol, β-nootkatol, β,γ-nootkatone, nootkatene, nootkatone and valencene. According to all disclosed embodiments, the raw material terpene blend may optionally include at least one compound or molecule that catalyzes the chemical reaction from nootkatol to nootkatene. According to all disclosed embodiments, the method may comprise adding to the raw material terpene blend containing the at least one nootkatol and the at least one compound or molecule that catalyzes the chemical reaction from nootkatol to nootkatene, an additional or further amounts of the compound(s) or molecule(s) that catalyze the chemical reaction from nootkatol to nootkatene. According to all disclosed embodiments, the method may comprise adding to the raw material terpene blend containing the at least one nootkatol and the at least one compound or molecule that catalyzes the chemical reaction from nootkatol to nootkatene, additional or further compound(s) or molecule(s) that catalyze the chemical reaction from nootkatol to nootkatene which are different in chemical structure from the at least one compound or molecule that catalyzes the chemical reaction from nootkatol to nootkatene already present within the raw material terpene blend.

According to certain embodiments, the raw material terpene blend may be prepared by microbial fermentation with suitable microbial organisms capable of carrying out the fermentation process to produce the terpene blend containing at least one nootkatol. The present disclosure is not limited to the use of terpene blends prepared by microbial fermentation, and raw material blends may contain nootkatols that have been extracted from grapefruit, Alaska yellow cedar trees, vetiver grasses, or compositions which contain sesquiterpene substrates, such as valencene, which can be oxidized to nootkatols by any means of oxidation, including, without limitation, chemical oxidation, enzymatic oxidation, or whole cell biotransformation. Methods of enzymatic oxidation of sesquiterpene substrates to oxygenated sesquiterpenes (for example, to nootkatol and/or nootkatone) are disclosed in WO 2016/029187 and WO 2016/029153, both of which are hereby incorporated by reference.

According to certain illustrative embodiments, the method for causing or inducing the conversion of nootkatol to nootkatene comprises adding one or more compounds that catalyze the chemical conversion of nootkatol to nootkatene to a feed comprising a raw material terpene blend containing nootkatol in the feed. The amount of the one or more compounds that catalyze the chemical conversion of nootkatol to nootkatene added to the raw material feed containing the terpene blend is a catalytically effective amount of the one or more compounds.

According to certain illustrative embodiments, the method of causing or inducing the conversion of nootkatol to nootkatene comprises providing a feed containing at least one nootkatol and adding a catalytically effective amount of one or more compounds that catalyze the chemical conversion of the nootkatol to nootkatene to a feed comprising a raw material terpene blend containing nootkatol in the feed.

According to certain illustrative embodiments, the method of causing or inducing the conversion of nootkatol to nootkatene comprises providing a feed containing at least one nootkatol and other desired terpene species, and adding one or more compounds that catalyze the chemical conversion of the nootkatol to nootkatene to a feed comprising a raw material terpene blend containing nootkatol in the feed.

According to certain illustrative embodiments, the method of causing or inducing the conversion of nootkatol to nootkatene comprises providing a feed containing at least one nootkatol other desired terpene species and an amount of at least one compound that catalyzes the conversion of nootkatol to nootkatene, and adding an additional amount of one or more compounds that catalyze the chemical conversion of nootkatol to nootkatene to a feed comprising a raw material terpene blend containing nootkatol in the feed.

According to certain illustrative embodiments, the method of causing or inducing the conversion of nootkatol to nootkatene comprises providing a feed containing at least one nootkatol such as nootkatol, adding a catalytically effective amount of one or more compounds that catalyze the chemical conversion of the nootkatol to nootkatene to a feed comprising a raw material terpene blend containing nootkatol in the feed, and subjecting the feed to reaction conditions effective to cause or induce conversion of nootkatol to nootkatene. Without limitation, the reaction conditions include heating the feed containing the nootkatol at a sufficient temperature for an effective amount of time with an effective amount of fatty acids to induce conversion of at least a portion of the nootkatol in the feed to nootkatene.

According to other illustrative embodiments, the method of causing or inducing the conversion of nootkatol to nootkatene comprises providing a feed containing at least one nootkatol, adding a catalytically effective amount of one or more compounds that catalyze the chemical conversion of the nootkatol to nootkatene to a feed comprising a raw material terpene blend containing nootkatol in the feed, and, and carrying out fractional distillation on the feed.

According to certain illustrative embodiments, the one or more compounds present in the feed materials that catalyzes the conversion of nootkatol to nootkatene comprises at least one acid. The acid may comprise any acid-containing molecule that catalyzes the conversion of nootkatol to nootkatene. The acids include inorganic (mineral) acids and organic acids. According to certain embodiments, the acid that catalyzes the conversion of nootkatol to nootkatene comprises a fatty acid. For example, and without limitation the fatty acid may comprise a carboxylic acid and a hydrocarbon tail having from 2 to 28 carbon atoms. The hydrocarbon tail may be straight or branched and may contain ring structures. This includes short chain fatty acids, medium chain fatty acids and long chain fatty acids. The fatty acids may be selected from saturated or unsaturated fatty acids. The hydrocarbon tails of the unsaturated fatty acids may contain one or more double bonds. The hydrogen atoms adjacent to the double bonds of the hydrocarbon tails of the unsaturated fatty acids may assume either the cis or trans configurations. According to certain embodiments, and without limitation, illustrative examples of the at least one fatty acid are selected from pelargonic acid (C9:0), capric acid (C10:0), undecanoic (C11:0), lauric acid (C12:0), tridecanoic acid (C13:0), myristic acid (C14:0), pentadecanoic acid (C15:0), palmitic acid (C16:0), linoleic acid (C18:2), oleic acid (C18:1), elaidic acid (C18:1), stearic acid (C18:0) and combinations thereof.

According to certain embodiments, the method of preparing a nootkatone composition comprises providing a feed containing at least one nootkatol. The feed is treated by adding a compound that causes or induces conversion of nootkatol to nootkatene. The treated feed is exposed to reaction conditions suitable for the catalytic conversion of nootkatol to nootkatene. In accordance with certain embodiments, by treating a feed containing nootkatol with a catalytically effective amount of at least one compound that catalyzes the chemical conversion of nootkatol to nootkatene, and subjecting the treated feed to reaction conditions sufficient for the conversion of at least a portion of the nootkatol to nootkatene, or by carrying out fractional distillation on the treated feed, a terpene blend containing 1 weight percent or greater nootkatene can be achieved.

A terpene blend may prepared by providing a feed containing at least one nootkatol, adding a catalytically effective amount of at least one compound capable of catalyzing the conversion of said at least one nootkatol to nootkatene and subjecting the feed to reaction conditions effective to convert at least a portion of said at least one nootkatol to nootkatene. According to certain illustrative embodiments, the terpene blend may comprise from about 0.1 to about 2.5 weight percent α-nootkatol, from about 0.001 to about 5 weight percent β-nootkatol, from about 0.1 to about 5 weight percent β,γ-nootkatone, from about 40 to about 560 weight percent nootkatone, from about 1 to about 5 weight percent nootkatene and from about 0.001 to about 15 weight percent valencene, based on the total weight of the terpene blend.

A terpene blend may be prepared by providing a feed containing at least one nootkatol, adding a catalytically effective amount of at least one compound capable of catalyzing the conversion of said at least one nootkatol to nootkatene, and carrying out fractional distillation on the feed. One or more fractions obtained from the fractional distillation step may be combined to form a terpene blend. According to certain illustrative embodiments, the terpene blend may comprise from about 0.1 to about 2.5 weight percent α-nootkatol, from about 0.001 to about 5 weight percent β-nootkatol, from about 0.1 to about 5 weight percent β,γ-nootkatone, from about 40 to about 560 weight percent nootkatone, from about 1 to about 5 weight percent nootkatene and from about 0.001 to about 15 weight percent valencene, based on the total weight of the terpene blend.

A fragrance composition containing the terpene blend prepared in accordance with the present disclosure may further include one or more additional fragrance compounds.

According to certain illustrative embodiments, without limitation, the additional fragrance compounds may include one or more aldehydic compound(s), one or more balsamic compound(s), one or more different citrus compound(s), one or more floral compound(s), one or more fruity compound(s), one or more gourmand compound(s), one or more green compound(s), one or more marine compound(s), one or more mossy compound(s), one or more musk compound(s), one or more piney compound(s), one or more spicy compound(s), and/or one or more woody compound (s), or combinations thereof.

By way of illustration, and not in limitation, suitable aldehydic compounds include saturated alkyl aldehydes including, but not limited to, ALDEHYDE C 12 MNA (2-methylundecanal); ALDEHYDE C 8 OCTYLIC (octanal); ALDEHYDE C 9 (nonanal); ALDEHYDE C 6 HEXYLIC (hexanal); CALYPSONE (6-methoxy-2,6-dimethyloctanal); ALDEHYDE C 7 HEPTYLIC (heptanal); ALDEHYDE C 10 decanal; ALDEHYDE C 12 dodecanal; acetaldehyde; n-butyraldehyde; isobutraldehyde. In one embodiment, the saturated alkyl aldehydes are selected from the group consisting of ALDEHYDE C 12 MNA and CALYPSONE.

In another embodiment, suitable odor-reducing materials include unsaturated alkyl aldehydes including, but not limited to, DECEN-1-AL, CIS-4 ((Z)-dec-4-enal); DECENAL-4-TRANS ((E)-dec-4-enal); DECENAL-9 (9-decenal), MELONAL (2,6-dimethylhept-5-enal); CYCLAL C (2,4-dimethylcyclohex-3-enecarbaldehyde); NONADIENAL ((2E,6Z)-nona-2,6-dienal); PINOACETALDEHYDE (3-(6,6-dimethylbicyclo[3.1.1]hept-2-en-2-yl)propanal); SHISOLIA (4-vinylcyclohex-1-enecarbaldehyde); MACEAL (bicyclo[2.2.2]oct-5-ene-2-carboxaldehyde); cinnamic aldehyde; citronellal; trans-2-hexenal; trans 2-decenal, cis-3-hexenal and cis-4-heptenal. In one embodiment, the unsaturated alkyl aldehydes are selected from the group consisting of MELONAL, CYCLAL C, SHISOLIA and MACEAL.

In another embodiment, suitable odor-reducing materials include aromatic aldehydes including, but not limited to, anisyl aldehyde; AUBEPINE PARA CRESOL (4-methoxybenzaldehyde), FLORHYDRAL (3-(3-isopropylphenyl)butanal); benzaldehyde; PHENYL PROPIONIC ALDEHYDE (3-phenylpropanal); and TOLYL ALDEHYDE PARA (4-methylbenzaldehyde).

By way of illustration, and not in limitation, suitable citrus compounds may include citral, citronellal, L-citronellol, decanal, limonene, myrcenol, sinensal, bergamot oil, grapefruit oil, lemon oil, lime oil, and/or orange oil.

By way of illustration, and not in limitation, suitable floral compound can be anisyl acetate, anisic aldehyde, benzyl acetate, bourgeonal, butyl acetate, cyclamen aldehyde, cyclohexyl lactone, delta-damascone, farnesal, L-farnesal, farnesol, florhydral, floralozone, geraniol, gernayl acetate, piperonal, hedione, heliobouquet, hexyl cinnamaldehyde, hexyl salicylate, indole, alpha-ionone, beta-ionone, isopropoxy ethyl salicylate, jasmodione, cis-jasmone, kovanol, laurinol, linalool, linalyl acetate, mayol, methyl dihydrojasomante, .gamma.-methyl ionone, methoxymelonal, nerol, nerolione, neryl acetate, 2-pentyl cyclopentanone, phenoxanol, phenoxy ethyl isobutyrate, phenylacetaldehyde, phenyl ethyl alcohol, rose oxide, suzaral, undecavertol, geranium oil, lavender oil, rose oil, and/or ylang oil. A fruity compound can be aldehyde C-C16, allyl caproate, allyl cyclohexyl proprionate, allyl heptanoate, amyl acetate, benzaldehyde, L-citronellyl acetate, L-citronellyl nitrile, cyclacet, damascenone, beta-decalactone, gamma-decalactone, diethyl malonate, dimethyl phenyl ethyl carbinol, dimethyl sulfide, gamma-dodecalactone, ethyl acetate, ethyl butyrate, ethyl caproate, ethyl decadienotate, ethyl-2-methylbutyrate, ethyl acetoacetate, ethyl propionate, florol, hexyl acetate, hexyl isobutyrate, isoamyl acetate, jasmolactone, manzanate, melonal, methyl heptyl ketone, gamma-nonalactone, gamma-octalactone, phenyl ethyl isobutyrate, raspberry ketone, ringonol, thesaron, tolyl aldehyde, gamma-undecalactone, vanoris, and/or verdox.

By way of illustration, and not in limitation, suitable gourmand compounds may include caprylic acid, coumarin, ethyl fraison, ethyl vanillin, ethyl maltol, filbertone, furaneol, guaiacol, maple furanone, 2-acetyl pyrazine, 2,5-dimethyl pyrazine, and/or vanillin.

By way of illustration, and not in limitation, suitable green compounds may include dynascone, galbanolene, trans-2-hexenal, cis-3-hexenol, hexen-1-ol, cis-3-hexenyl acetate, cis-3-hexenyl butyrate, cis-3-hexenyl salicyclate, liffarome, methyl octine carbonate, 2,6-nonadienal, oxane, stemone, styrallyl acetate, triplal, undecavertol, violet methyl carbonate, vionil, and/or violet leaf extract.

By way of illustration, and not in limitation, suitable musk compounds may include ambrettolide, ambretone, ambroxan, exaltolide, galaxolide, habanolide, helvetolide, (1'R)-3-methyl-5-(2,2,3-trimethylcyclopentan-1-yl)-2-pentanone, muscenone, musk T, L-muscone, and/or tonalid.

By way of illustration, and not in limitation, suitable piney compounds may include alpha-pinene, beta-pinene and mixture thereof.

By way of illustration, and not in limitation, suitable spicy compounds may include .beta.-caryophellene, cinnamaldehyde, cuminaldehyde, eugenol, isoeugenol, perilla aldehyde, cardamom oil, clove oil, ginger extract and/or black pepper extract.

By way of illustration, and not in limitation, suitable woody compounds may include amber core, amber extreme, ambroxan, bacdanol, cedramber, cedanol, ebanol, hindinol, hinokitiol, javanol, norlimbanol dextro, osyrol, patchone, polyambrol, .alpha.-pinene, .beta.-pinene, sandalmysore core, sandalore, santalex T, orbitone, cedarwood oil, patchouli oil, sandalwood oil, and/or vetiver oil.

The terpene blend of the present disclosure may be included in a wide variety of food and beverage products.

The terpene blend of the present disclosure may be included in a wide variety of foods products that would benefit from a citrus aroma and/or flavour.

Muffins (e.g., English muffins), crackers (e.g., salted crackers, baked crackers, graham crackers, etc.), rolls (e.g., soft rolls, dinner rolls, crescent rolls), biscuits (e.g., buttermilk biscuits, cobbler biscuits), pie crusts, breads (e.g., focaccia, bruschetta, sourdough breads, soda breads, breadsticks, corn bread, etc.), bagels, brownies, cookies, turnovers, doughnuts, cakes, pastries, pies, scones, and the like.

Without limitation, and only by way of illustration, exemplary dairy products include ice cream, impulse ice cream, ice cream desserts, frozen yoghurt, milk, fresh/pasteurized milk, full fat fresh/pasteurized milk, semi skimmed fresh/pasteurized milk, long-life/UHT milk, full fat long life/UHT milk, semi skimmed long life/UHT milk, fat-free long life/UHT milk, goat milk, condensed/evaporated milk, plain condensed/evaporated milk, flavoured, functional and other condensed milk, flavoured milk drinks, dairy only flavoured milk drinks, soy milk, sour milk drinks, fermented dairy drinks, coffee creamers/whiteners, powder milk, flavoured powder milk drinks, cream, yoghurt, plain/natural yoghurt, flavoured yoghurt, fruited yoghurt, probiotic yoghurt, yoghurt drinks, and other dairy-based desserts.

Without limitation, and only by way of limitation, exemplary savoury food products include, salty snacks (potato chips, crisps, nuts, tortilla-tostada, pretzels, cheese snacks, corn snacks, potato-snacks, ready-to-eat popcorn, microwaveable popcorn, pork rinds, nuts, crackers, cracker snacks, breakfast cereals, meats, cured meats, luncheon/breakfast meats, tomato products, peanut butter, soups, canned vegetables, pasta sauces, and savoury biscuits, crackers and bread substitutes.

Without limitation, and only by way of illustration, sweet products include breakfast cereals, ready-to-eat ("rte") cereals, family breakfast cereals, flakes, muesli, other rte cereals, children's breakfast cereals, and hot cereals.

The terpene blend and/or flavour compositions including the terpene blend of the present disclosure may be included in citrus beverages. Suitable citrus beverages include, without limitation, alcoholic citrus cocktails, citrus-flavoured drinks, citrus liqueurs, citrus-flavoured sodas, citrus-flavoured soft drinks, citrus-flavoured waters, citrus-flavoured still water, citrus-flavoured carbonated water, and the like. The terpene blend and/or flavour compositions including the terpene blend of the present disclosure may be included in tropical flavour compositions or foods and beverages containing tropical flavours (such as, for example, coconut, guava, kiwi, mango, papaya, passion fruit and pineapple flavour) containing citrus components.

The terpene blends and flavour compositions containing the terpene blends may be used in personal care products such as pharmaceuticals, cosmetics, and toiletries.

When used within cosmetics and toiletries, the formulations can be used in any of the "Reported Product Categories" listed by the Cosmetic, Toiletries and Fragrance Association's 'International Cosmetic Ingredient Dictionary and Handbook', and with any one or more of the ingredients cited as being used for the reported product categories. The Reported Product Categories include: aftershave lotions, baby lotions, oils, powders and creams, baby products miscellaneous, baby shampoos, basecoats and undercoats, bath capsules, bath oils, tablets and salts, bath preparations miscellaneous, bath soaps and detergents, beard softeners, blushers, body and hand preparations, bubble baths, cleaning products, colognes and toilet waters, cuticle softeners, dentifrices, deodorants, depilatories, douches, eye lotions, eye makeup preparations miscellaneous, eye makeup removers, eye shadows, eyebrow pencils, eyeliners, face and neck preparations, face powders, feminine hygiene deodorants, foot powders and sprays, foundations, fragrance preparations miscellaneous, hair bleaches, hair colour sprays, hair colouring preparations miscellaneous, hair conditioners, hair dyes and colours, hair lighteners with colour, hair preparations, hair rinses, hair shampoos, hair sprays, hair straighteners, hair tints, hair wave sets, indoor tanning preparations, leg and body paints, lipsticks, makeup bases, makeup fixatives, makeup preparations, manicuring preparations miscellaneous, mascara, men's talcum, moisturising preparations, mouthwashes and breath fresheners, nail creams and lotions, nail extenders, nail polish and enamel removers, nail polish and enamels, night skin care preparations, oral hygiene products miscellaneous, paste masks, perfumes, permanent waves, personal cleanliness products miscellaneous, powders, preshave lotions, rouges, sachets, shampoos, shaving cream, shaving preparations miscellaneous, shaving soap, skin care preparations miscellaneous, skin fresheners, suntan gels, creams and liquids, suntan preparations miscellaneous, sonics, dressings and other hair grooming aids.

The "oral care" or "oral hygiene" products may include any product that is applied to the oral cavity for the purposes of cleaning, freshening, healing, deodorizing the oral cavity or any part thereof. Without limitation, and only by way of illustration, such oral care and oral hygiene compositions include, toothpastes, tooth gels, tooth powders, tooth whitening products, mouth rinses, mouthwashes, gargle compositions, lozenges, dental floss, tooth picks, anti-plaque and anti-gingivitis compositions, throat lozenges, throat drops, compositions for treatment of nasal symptoms, cold symptoms, and for cold relief.

The nootkatone oil composition of the present disclosure may be included in a wide variety of other consumer products. Without limitation, and only by way of illustration, the consumer product may be selected from a fine fragrance, a home care product, and an air care product.

According to certain illustrative embodiments, and without limitation, the fine fragrance product may be selected from parfum, extrait de parfum, eau de parfum, millesime, parfum de toilette, eau de toilette, eau de cologne, body splash, after shave, body mists, and baby colognes.

According to certain illustrative embodiments, and without limitation, the home care product may be selected from fabric conditioner, fabric softener, laundry detergent, laundry additive, rinse additive, bleach, dryer sheets, perfume beads, car care products, dishwashing detergent, and hard surface cleaners.

According to certain illustrative embodiments, and without limitation, the air care product may be selected from a candle, aerosol, air freshener, liquid electric air freshener, fragrance diffuser, gel air freshener, plug-in air freshener, plug-in oil, and wax melt.

EXAMPLES

The following examples are set forth to describe illustrative embodiments of the disclosed methods in further detail and to illustrate the methods of mitigating or preventing the conversion of α-nootkatol to nootkatene in a terpene blend. The examples should not be construed as limiting the mitigating the chemical conversion of α-nootkatol to nootkatene in terpene blend feed, methods of making terpene blends, terpene blends, flavour compositions, fragrance compositions, beverage products, food products, fragrance products, methods of making beverage products, methods of making food products, and methods of making fragranced products

Comparative Example 1

A raw material blend of citrus terpenes containing an insufficient amount of total fatty acids to cause the conversion of α-nootkatol to nootkatene was fractionally distilled under full vacuum for 90 minutes. Table 1 below shows the initial amount of each of the components of the raw material terpene blend, and the amount of each component that was recovered from a high temperature fractional distillation process typically used to prepare nootkatone blends for use as flavour and fragrance ingredient. As shown in Table 1, 100% (76.6 g) of α-nootkatol initially charged into the flask was recovered following the distillation process. The amount of nootkatene recovered was 102% (9.6 g), which results only a 2% increase in the amount of nootkatene formed during the distillation process.

TABLE 1

|  | Valencene | Alpha-Nootkatol | Beta-Nootkatol | Beta-Gamma Nootkatone | Nootkatene | Nootkatone | Other |
|---|---|---|---|---|---|---|---|
| Sample charged to flask (g): | 132.0 | 76.5 | 1.9 | 0.0 | 9.4 | 257.9 | 272 |
| Recovered (g): | 131.3 | 76.6 | 2.1 | 0.0 | 9.6 | 254.6 | 255 |
| Distillate yield (%): | 99% | 100% | 109% | 0% | 102% | 99% | 94% |

Example 2

A sample of the same raw material blend of citrus terpenes used in Comparative Example 1 with an addition of 2% safflower oil was fractionally distilled under full vacuum for 90 minutes. Table 2 below shows the initial amount of each of the components of the raw material terpene blend, and the amount of each component that was recovered from a high temperature fractional distillation process typically used to prepare nootkatone blends for use as flavour and fragrance ingredient. As shown in Table 2, only 78% (46.5 g) of α-nootkatol initially charged into the flask was recovered following the distillation process and 22% was consumed during the distillation. The amount of nootkatene recovered was 143% (9.6 g), which represents a 43% increase in the amount of nootkatene formed during the distillation process.

TABLE 2

|  | Valencene | Alpha-Nootkatol | Beta-Nootkatol | Beta-Gamma Nootkatone | Nootkatene | Nootkatone | Other |
|---|---|---|---|---|---|---|---|
| Sample charged to flask (g): | 95.1 | 59.8 | 1.6 | 0.0 | 6.7 | 183.4 | 173 |
| Recovered (g): | 86.7 | 46.5 | 1.6 | 0.0 | 9.6 | 152.4 | 159 |
| Distillate yield (%): | 91% | 78% | 97% | 0% | 143% | 83% | 92% |

It should be understood that when a range of values is described in the present disclosure, it is intended that any and every value within the range, including the end points, is to be considered as having been disclosed. For example, "a range of from 50 to 100" of a component is to be read as indicating each and every possible number along the continuum between 50 and 100. It is to be understood that the inventors appreciate and understand that any and all values within the range are to be considered to have been specified, and that the inventors have possession of the entire range and all the values within the range.

In the present disclosure, the term "about" used in connection with a value is inclusive of the stated value and has the meaning dictated by the context. For example, it includes at least the degree of error associated with the measurement of the particular value. One of ordinary skill in the art would understand the term "about" is used herein to mean that an amount of "about" of a recited value produces the desired degree of effectiveness in the compositions and/or methods of the present disclosure. One of ordinary skill in the art would further understand that the metes and bounds of "about" with respect to the value of a percentage, amount or quantity of any component in an embodiment can be determined by varying the value, determining the effectiveness of the compositions for each value, and determining the range of values that produce compositions with the desired degree of effectiveness in accordance with the present disclosure. The term "about" is further used to reflect the possibility that a composition may contain trace components of other materials that do not alter the effectiveness or safety of the composition.

Any compositional weight percentages disclosed herein are based on the total weight of the terpene blends, flavour compositions, fragrance compositions, food products, beverage products, or fragranced products, as the situation dictates. It will be understood to one of ordinary skill in the art that the total weight percent of the particular blend, composition or product cannot exceed 100%. For example, a person of ordinary skill in the art would easily recognize and understand that a beverage product comprising 50 to 95 weight percent of a beverage base and 5 to 50 weight percent of a terpene-based flavour composition will not exceed 100%. A person of ordinary skill in the art would understand that the amount of the components may be adjusted to include the desired amount of component without exceeding 100% by weight of the blends, compositions, or products.

The foregoing text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein.

While the methods of causing the chemical conversion of nootkatol to nootkatene in terpene blend feed, methods of making terpene blends, terpene blends, flavour compositions, fragrance compositions, beverage products, food products, fragrance products, methods of making beverage products, methods of making food products, and methods of making fragranced products have been described in connection with various illustrative embodiments, it is to be understood that other similar embodiments may be used or modifications and additions may be made to the described embodiments for performing the same function. Furthermore, the various illustrative embodiments may be combined to produce the desired results. Therefore, the methods of the chemical conversion of nootkatol to nootkatene in terpene blend feed, methods of making terpene blends, terpene blends, flavour compositions, fragrance compositions, beverage products, food products and fragrance products should not be limited to any single embodiment, but rather construed in breadth and scope in accordance with the recitation of the appended claims. It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

The invention claimed is:

1. A method of causing or inducing the conversion of nootkatol to nootkatene comprising:
   providing a feed containing nootkatol; and
   adding a catalytically effective amount of at least one compound that catalyzes the conversion of α-nootkatol to nootkatene in the feed.

2. The method of causing or inducing the conversion of nootkatol to nootkatene of claim 1, wherein the feed comprises a blend of volatile terpenes including α-nootkatol and at least one other volatile terpene.

3. The method of causing or inducing the conversion of nootkatol to nootkatene of claim 1, wherein the compound that catalyzes the conversion of nootkatol to nootkatene comprises an acid.

4. The method of causing or inducing the conversion of nootkatol to nootkatene of claim 3, wherein the acid comprises at least one fatty acid.

5. The method of causing or inducing the conversion of nootkatol to nootkatene of claim 4, wherein the at least one fatty acid is selected from saturated and unsaturated fatty acids having 2 to 28 carbon atoms.

6. A method of preparing a terpene blend comprising:
   providing a feed containing at least one nootkatol;
   adding a catalytically effective amount of at least one compound to catalyze the conversion of said at least one nootkatol to nootkatene; and
   carrying out fractional distillation on the feed to recover compounds comprising α-nootkatol, β-nootkatol, nootkatene, nootkatone, and valencene.

7. The method of preparing the terpene blend of claim 6, wherein the feed comprises a blend of volatile terpenes including α-nootkatol.

8. The method of preparing the terpene blend of claim 6, wherein the feed comprises a blend of volatile terpenes including α-nootkatol and β-nootkatol.

9. The method of preparing the terpene blend of claim 6, wherein the compound that catalyzes the conversion of nootkatol to nootkatene comprises at least one acid.

10. The method of preparing the terpene blend of claim 9, wherein the at least one acid comprises as least one fatty acid.

* * * * *